United States Patent [19]

Chandler

[11] Patent Number: 5,554,313
[45] Date of Patent: Sep. 10, 1996

[54] CONDITIONING SHAMPOO CONTAINING INSOLUBLE, NONVOLATILE SILICONE

[75] Inventor: John M. Chandler, Bear, Del.

[73] Assignee: ICI Americas Inc., Wilmington, Del.

[21] Appl. No.: 267,692

[22] Filed: Jun. 28, 1994

[51] Int. Cl.[6] .................................................. A61K 7/075
[52] U.S. Cl. .................. 510/121; 424/70.12; 424/70.19; 424/70.31; 510/122; 510/535; 510/537; 510/466; 510/128; 510/417; 510/505; 252/312
[58] Field of Search ...................................... 252/173, 174, 252/174.15, 174.21, DIG. 13, DIG. 14, 544, 550; 424/70.1, 70.19, 70.21, 70.22, 70.27, 70.31, 70.12

[56] References Cited

U.S. PATENT DOCUMENTS

| | | |
|---|---|---|
| 3,964,500 | 6/1976 | Drakoff . |
| 4,427,557 | 1/1984 | Stockburger . |
| 4,465,619 | 8/1984 | Boskamp . |
| 4,704,272 | 11/1987 | Oh et al. . |
| 4,728,457 | 3/1988 | Fieler et al. . |
| 4,749,732 | 6/1988 | Kohl et al. . |
| 4,842,850 | 6/1989 | Vu . |
| 5,011,681 | 4/1991 | Ciotti et al. ............................... 424/81 |
| 5,015,415 | 5/1991 | Goze et al. . |
| 5,034,218 | 7/1991 | Duvel . |
| 5,063,044 | 11/1991 | Kohl et al. . |

FOREIGN PATENT DOCUMENTS 2245279A  1/1992  United Kingdom .

OTHER PUBLICATIONS

"Multifunctional Shampoos," Branko Sajic and Irene Shapiro, Cosmetics & Toiletries, vol. 107, May 1992, pp. 103–107.

*Primary Examiner*—Margaret Einsmann
*Attorney, Agent, or Firm*—John M. Sheehan

[57] ABSTRACT

The present invention relates to shampoo compositions and more particularly shampoo compositions containing nonvolatile silicone materials and methods of making the same. Specifically, this invention is directed to aqueous shampoo compositions comprising sorbitan stearate, sorbitan distearate or mixtures thereof; stearyl alcohol ethoxylates, insoluble non-volatile silicone, and combinations of surfactants selected from anionic, nonionic and amphoteric surfactants. This invention also relates to a method of forming a aqueous shampoo composition comprising insoluble, nonvolatile silicone by the method of forming a preformed aqueous silicone emulsion and combining with a combination of surfactants.

20 Claims, No Drawings

CONDITIONING SHAMPOO CONTAINING INSOLUBLE, NONVOLATILE SILICONE

BACKGROUND OF THE INVENTION

The present invention relates to shampoo compositions, and more particularly to shampoo compositions containing non-volatile silicone materials which condition the hair leaving it softer and more manageable.

When washing the hair with conventional shampoo compositions, the natural oils are removed together with the dirt and unwanted oils. When too much of the natural oil is removed, for example by especially frequent washing, the hair becomes less easy to comb or style, and subject to static build-up causing "flyaway."

Hair conditioners have been developed to try to restore the condition of the hair. These compositions are normally applied to hair after shampooing, left on the hair for a period of time and rinsed off. This process is time consuming and expensive since two separate products are needed.

During the mid-to-late 1980's, 2-in-1 conditioning shampoos have risen in popularity due to their convenience. Many brands now carry a conditioning version as part of their line. Conditioning shampoos present challenges to the formulator. Incorporating such conditioning agents as quaternary ammonium compounds, synthetic cationic polymers, and silicones into shampoo bases can be difficult. Also, deriving benefits from these conditioning agents when formulated into a shampoo base is troublesome.

Quaternary ammonium compounds are often incompatible with anionic shampoo ingredients. Even when they are successfully incorporated into a shampoo, their effectiveness is questioned. Synthetic cationic polymers have been used in anionic shampoo systems with some success, yet many tend to build up on the hair after repeated applications, and these materials' primary effect is directed more toward increasing manageability rather than wet and dry combing smoothness which is looked for in the standard 2-in-1 shampoo. Other conditioning shampoos employ such water soluble silicone materials as dimethicone copolyols yet they are believed to be less effective than insoluble silicones. The higher molecular weight insoluble, nonvolatile silicones are difficult to handle and most difficult to incorporate into a shampoo yet give optimum results on wet and dry hair.

Some conditioning 2-in-1 shampoo formulas have been developed which use a dispersion technique (see U.S. Pat. Nos. 4,704,272, 4,728,457, 4,788,272, and 5,085,857) to keep the insoluble, nonvolatile silicone from separating out of the shampoo. The practice of these patents in a number of popular shampoos employs Xanthan Gum to disperse the silicone. The problem with these types of shampoos is they present significant challenges to the skilled formulator.

It is generally believed in the industry that insoluble, nonvolatile silicones can not be emulsified directly into shampoo composition due to the generally high HLB value of anionic and amphoteric shampoo compositions and low required HLB of such silicones. (HLB stands for 'Hydrophile-Lipophile Balance' and is a measure of the relative proportions of water-soluble and oil soluble components in a surfactant; see Griffin, W. C., J. Soc. Cosmetic Chemists 1949, 1311 and "Emulsions: Theory and Practice," p. 232 ff (P. Becher, Reinhold, 1965). For any given surfactant function, such as detergency, emulsification or wetting, there is usually an optimum HLB value.) Current emulsion technology dictates that the surfactants' HLB in a system must match the HLB requirement of the insoluble materials (i.e. silicone).

Nonionic surfactant based shampoos, without anionic or amphoteric surfactants, enable incorporation of higher levels of cationic materials and are able to be blended to the low HLB requirements of an insoluble, nonvolatile silicone. However, these systems are not favored because of the low foaming and high sebum stripping effects associated with predominantly nonionic detergent systems.

Non-volatile silicone oils are useful as conditioning agents, but again excessive amounts of silicone can dull the hair, and build-up of silicone on the hair can give a greasy appearance. Furthermore, the incorporation of silicone oil generally gives an antifoam effect.

We have found that the combination of an aqueous emulsion of a silicone oil conditioner in a surfactant-based composition will impart improved conditioning benefit to the hair with none of the undesirable dulling effects or greasy build-up seen with other conditioning products, and without the need for a two-step washing and conditioning procedure.

Accordingly, the invention provides an aqueous composition comprising, in addition to water, a mixture of emulsifiers, a insoluble, non-volatile silicone and a mixture of detergent surfactants.

A still further aspect, this invention provides a stable shampoo composition comprising a insoluble, non-volatile silicone without the presence of a Xanthan gum.

In addition, this invention provides a stable composition comprising an emulsified insoluble, non-volatile silicone having an HLB value greater than the HLB requirement specified for such silicone.

This invention also provides a method of making a stable composition comprising an emulsion of insoluble, non-volatile silicone in a aqueous solution having a much higher HLB value than theoretically specified for such silicone whereby the silicone is emulsified in an aqueous solution at the specified HLB value for such silicone. Then detergent surfactants are added tending to increase the HLB level while the silicone remains emulsified.

DETAILED DESCRIPTION OF THE INVENTION

(a) Surfactant

The composition according to the invention comprises a surfactant chosen from anionic, nonionic or amphoteric surfactant or mixtures thereof.

Suitable anionic surfactants are the alkyl ether sulphates, N-alkoyl sarcosinates, alkyl phosphates, alkyl ether phosphates and especially their sodium, magnesium, ammonium and mono-, di and triethanolamine salts. The alkyl groups generally contain from 8 to 18 carbon atoms and may be unsaturated. The alkyl ether sulphates and alkyl ether phosphates may contain from one to 10 ethylene oxide or propylene oxide units per molecule, and preferably contain 2 to 3 ethylene oxide units per molecule.

Examples of suitable anionic surfactants include sodium N-lauryl sarcosinate. The most preferred anionic surfactant are sodium lauryl sulphate, sodium lauryl n-(ethylene oxide) sulphate where n is 1 to 3.

The nonionic surfactants suitable for use in the composition of the invention may include condensation products of aliphatic ($C_8$–$C_{18}$) primary or secondary linear or branched chain alcohols or phenols with alkylene oxides, usually comprising 6–30 ethylene oxide units.

Other suitable nonionics include mono or di alkyl alkanolamides or alkyl polyglucosides. Examples include coco mono or diethanolamide, including cocamide diethanol amide, coco mono isopropanolamide, and coco di glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates (including those which have the CTFA designation disodium coco amphodiacetates), alkyl amphopropionates, alkyl amidopropyl hydroxysultaines, acyl taurates and acyl glutamates wherein the alkyl and acyl groups have from 8 to 18 carbon atoms. Examples include lauryl amine oxide and cocodimethyl sulphopropyl betaine and the preferred amphoteric surfactants of the present composition are disodium lauroamphodiacetate and cocoamidopropyl betaine.

The surfactants are present in the shampoo composition of the invention in an amount of from 1 to 40% by weight of the composition, typically 5 to 25% by weight of the composition and preferably from 10 to 17% by weight of the composition.

(b) Silicone

The shampoo composition of the invention also comprises an insoluble, non-volatile silicone, which may be one or more polyalkyl siloxanes, one or more polyalkylaryl siloxanes, or mixtures thereof. The silicone is insoluble in the aqueous matrix of the composition and so is present in an emulsified form.

Suitable polyalkyl siloxanes include polydimethyl siloxanes which have the CTFA designation dimethicone, having a viscosity of from 5 to 500,000 centistokes, typically 20,000 to 200,00 and preferably 50,000 to 150,000 at 25 C. These siloxanes are available commercially from the General Electric Company as the Viscasil series or from Dow Corning as the DC 200 series. The viscosity can be measured by means of a glass capillary viscometer as set out further in Dow Corning Corporation Test Method CTM004 Jul. 20, 1970.

Also suitable is polydiethyl silcoxane.

The polyalkylaryl siloxanes which may be used in the compositions of the invention include polymethylphenyl polysiloxanes having a viscosity of from 15 to 65 centistokes at 25 C. These siloxanes are available commercially from the General Electric Company as SF 1075 methyl phenyl fluid or from Dow Corning as 556 Cosmetic Grade Fluid.

Also suitable are silicone gums, such as those described in U.S. Pat. No. 4,152,416 (Spitzer), and on General Electric Silicone Rubber product. Data Sheet SE 30, SE 33, SE 54 and SE 75. "Silicone gum" denotes polydiorganosiloxanes having a molecular weight of from 200,000 to 1,000,000, and specific examples include polydimethyl siloxane polymer, polydimethyl siloxane/diphenyl/methylvinylsiloxane copolymer, polydimethylsiloxane/methylvinylsiloxane copolymer and mixtures thereof.

The silicone materials described above are preferably incorporated in the shampoo composition of the invention as a preformed aqueous emulsion. The emulsion may be prepared by emulsifying the insoluble, non-volatile silicone with water and an emulsifier or mixtures of emulsifiers—mixing the silicone into a heated solution of the emulsifier.

Suitable emulsifiers include sorbitan stearate, sorbitan distearate and mixtures thereof and therebetween. Preferred emulsifiers are sorbitan monostearate available commercially from ICI Americas Inc. as SPAN® 60 surfactant.

Also suitable are nonionic emulsifiers such as stearyl alcohol ethoxylates e.g. stearyl alcohol nEO, where n is at least 50, and does not exceed 130, typically n is between 75 and 110. Preferably the nonionic emulsifier is polyoxyethylene 100 stearyl ether available commercially from ICI Americas Inc. as BRIJ® 700S surfactant.

The balance of the aqueous composition is water. Water is typically present in the composition between 45 to 95% by weight of the composition, although it can be as much as 99% by weight of the composition. More typically, water is present in the composition at an amount of at least 60% by weight of the composition, preferably at an amount of at least 70% by weight of the composition.

Typically, a pre-formed emulsion will contain between 0.1 to 15% silicone, more typically 2 to 5% by weight of the emulsion. The overall compositions of the invention contains from 0.01 to 10% by weight, preferably from 0.1 to 5% by weight, of insoluble, nonvolatile silicone. If less than 0.01% by weight is present in the composition, little conditioning benefit is observed, and if more than 10% by weight is present, the hair will appear greasy.

The aqueous pre-formed emulsion may be incorporated into the shampoo composition in an amount of from 50 to 95% by weight, typically between 60 and 80% by weight, preferably from 65 to 75% by weight.

The exact quantity of emulsion will of course depend on the concentration of the emulsion, and should be selected to give the desired quantity of insoluble, nonvolatile silicone in the final composition.

The composition of this invention can be formed by mixing, at an elevated temperature, the sorbitan emulsifiers and the other nonionic emulsifiers in water, followed by the addition of the insoluble, non-volatile silicone, to form a pre-formed aqueous emulsion. This emulsifier system has an HLB value in the range of the silicone HLB requirement which is typically between 3 and 8, preferably 4 and 7. This preformed aqueous emulsion is then mixed, at a lower temperature with suitable anionic, nonionic and/or amphoteric detergent surfactants which tend to elevate the HLB value to a value typically between 12 and 40, preferably between 16 and 25.

The emulsified insoluble, non-volatile silicone in the final composition has an average particle size typically between 20 and 50 microns and preferably between 25 and 40 microns.

OTHER INGREDIENTS

The shampoo composition of the invention may also include minor amounts of other ingredients commonly found in shampoo compositions, such as antibacterial agents, antidandruff agents such as zinc pyridinethione or Octopirox, a shear thinning polymer, such as a cross linked polyacrylate or an insoluble solid which forms a network within the composition, guar gums or derivatives thereof, foam boosters, pearlescers, such as ethylene glycol distearate, perfumes, dyes, coloring agents, conditioning agents, preservatives, viscosity modifiers, proteins, polymers, buffering agents, polyols and other moisturizing agents, herb extracts, mink oil and/or honey.

The shampoo composition may also optional include a guar gum or guar gum derivative component as a stabilizing and/or conditioning agent. Typically these guar gum components are present in an amount of less than 5% by weight of the composition, more typically in an amount of less than 0.005% by weight of the composition.

USE OF THE COMPOSITION

The shampoo composition of the invention may be applied in an amount of from 3 to 5 ml to wet hair. The wet hair is worked to create a lather. The lather may be retained on the head for a short time before rinsing e.g. from 1 to 4 minutes, or may immediately be rinsed. The washing procedure may be repeated if required.

The hair is generally found to be clean, manageable and easily combed and styled, without the need for a further conditioning step.

EXAMPLES

In the examples unless otherwise specified all percentages are given in percent by weight of the total composition.

Preparation A

A preformed aqueous emulsion

About 64% water, about 2.94% sorbitan monosterate, and about 0.06% polyoxyethylene 100 stearyl ether were heated up under gentle agitation. At about 80 C. the mixture was vigorously agitated for about one minute. The mixture was then allowed to cool under gentle agitation to about 70 C. About 3% by weight of dimethicone having a viscosity of about 100,000 centistokes at 25 C. was slowly mixed into such mixture with moderate stirring. The mixture continued to cool under gentle agitation until about room temperature.

Example 1

The following surfactants and water were sequentially added to Preparation A at the following percentages. (1) About 11% aqueous sodium laureth sulfate (70% active)*, (2) about 10% aqueous cocoamidopropyl betaine (30% active)*, (3) about 6% water and (4) about 3% cocamide diethanolamide (cocamide DEA) were added at about room temperature under moderate stirring.

Examples 2–4

Examples 2–4 were prepared using Preparation A and a procedure similar to those as described in Example 1 with the quantities and types of detergent surfactants and water being varied as summarized in Table 1. Note the additives are listed in the order of addition into the composition.

TABLE 1

| | Additive | % by weight |
|---|---|---|
| Example 2 | Sodium Lauryl Sulfate | 4 |
| | Sodium Laureth Sulfate (70% active)* | 7 |
| | Disodium lauroamphodiacetate (40% active)* | 4 |
| | WATER | 9 |
| | Cocoamidopropyl betaine (30% active)* | 3 |
| | Cocamide DEA | 3 |
| Example 3 | Sodium Lauryl Sulfate (70% active)* | 5 |
| | Sodium Laureth Sulfate (70% active)* | 10 |
| | Disodium laureth-3 sulfosuccinate (30% active)* | 3 |
| | Sodium cocyl sarcosinate (30% active)* | 4 |
| | Cocoamidopropyl betaine (30% active)* | 5 |
| | Cocamide DEA | 3 |

TABLE 1-continued

| | Additive | % by weight |
|---|---|---|
| Example 4 | TEA lauryl sulfate (40% active)* | 5 |
| | Sodium Trideceth Sulfate (70% active)* | 5 |
| | Disodium laureth-3 sulfosuccinate (30% active)* | 5 |
| | Cocoamphodiacetate (30% active)* | 5 |
| | WATER | 8 |
| | Cocamide DEA | 2 |

*Note: The percent activity indicates that the surfactant is present at that amount by weight in an aqueous solution with the balance water.

The foaming propensity of these compositions were measured by preparing a 200 ml aqueous solution with 2% by weight of the composition in a Waring Blendor for 10 seconds on the high setting then measuring the foam height. The results of these tests are summarized in Table 2.

TABLE 2

| Example No. | Foam Height (mm) |
|---|---|
| 1 | 770 |
| 2 | 760 |
| 3 | 870 |
| 4 | 660 |

What is claimed is:

1. An aqueous composition comprising:

(a) from 45 to 95%, by weight of the composition, water;

(b) from 1 to 5%, by weight of the composition, sorbitan monosterate, sorbitan distearate or mixtures thereof;

(c) from 0.01 to 1%, by weight of the composition, stearyl alcohol ethylene oxide condensate having at least 50 and does not exceed 13 ethylene oxide units;

(d) from 0.1 to 10%, by weight of the composition, insoluble, non-volatile silicone; and (e) from 1 to 40% by weight of the composition, surfactant or combinations of surfactants selected from the group consisting of:

i. anionic surfactants or combinations thereof selected from the group consisting of sodium, magnesium, ammonium and mono-, di- and triethanolamine salts of alkyl ether sulfates, N-alkoyl sarcosinates, alkyl phosphates, and alkyl ether phosphates;

ii. nonionic surfactants or combinations thereof selected from aliphatic ($C_8$–$C_{18}$) primary or secondary, linear or branched chain alcohols and phenols condensed with 60 to 30 alkylene oxide units and mono or dialkyl alkanolamides or alkyl polyglucosides;

iii. amphoteric surfactants or combinations thereof; and iv. mixtures thereof.

2. The aqueous composition of claim 1 wherein the surfactants are present in an amount from 5 to 25% by weight of the composition.

3. The aqueous composition of claim 1 wherein guar gum or guar gum derivatives are added in an amount of less than 0.005%.

4. The aqueous composition of claim 1 wherein component (b) is sorbitan monosterate.

5. The aqueous composition of claim 4 wherein component (c) is polyoxyethylene 100 stearyl ether.

6. The aqueous composition of claim of 2 wherein component:

(b) is sorbitan monostearate;
(c) is stearyl alcohol ethylene oxide condensate having 100 moles of ethylene oxide per mole of stearyl alcohol;
(d) is dimethicone having a viscosity of from 5 to 500,000 centistokes at 25° C.

7. An aqueous composition comprising:
   (a) a preformed aqueous-silicone emulsion comprising:
      i. 70 to 95%, by weight of the composition, of water
      ii. 1 to 5%, by weight of the composition, of sorbitan stearate, sorbitan distearate or mixtures thereof;
      iii. 0.001 to 1%, by weight of the composition, of stearyl alcohol ethylene oxide condensate having at least 50 and does not exceed 130 moles of ethylene oxide per mole of stearyl alcohol; and
      iv. 0.01 to 10%, by weight of the composition, of an insoluble, non-volatile silicone; and
   (b) a surfactant or a combination of surfactants selected from the group consisting of:
      i. anionic surfactants or combinations thereof selected from the group consisting of sodium, magnesium, ammonium and mono-, di- and triethanol amine salts of alkyl ether sulfates, N-alkoyl sarcosinates, alkyl phosphates, and alkyl ether phosphates;
      ii. nonionic surfactants or combinations thereof selected from aliphatic ($C_8$–$C_{18}$) primary or secondary, linear or branched chain alcohols and phenols condensed with 60 to 30 alkylene oxide units and mono or dialkyl alkanolamides or alkyl polyglucosides;
      iii. amphoteric surfactants or combinations thereof; and
      iv. mixtures thereof.

8. The aqueous composition of claim 7 wherein the preformed emulsion contains from 0.1 to 5% by weight of the composition of non-volatile, insoluble silicone.

9. The aqueous composition of claim 7 wherein component (b) is present in an amount of 1 to 40% by weight of the total composition.

10. The aqueous composition of claim 7 wherein the average particle size of the silicone material present in the emulsion is between 20 and 50 microns.

11. The aqueous composition of claim 7 wherein the performed emulsion has an emulsifier HLB value between 3 and 8.

12. A method of making an aqueous composition comprising: mixing together
   (a) a preformed emulsion formed by combining:
      i. 70 to 95%, by weight of the composition, of water
      ii. 1 to 5%, by weight of the composition, of sorbitan stearate, sorbitan distearate or mixtures thereof;
      iii. 0.001 to 1%, by weight of the composition, of stearyl alcohol ethylene oxide condensate having at least 50 and does not exceed 130 moles of ethylene oxide per mole of stearyl alcohol; and
      iv. 0.01 to 10%, by weight of the composition, of an insoluble, non-volatile silicone; and
   (b) a surfactant or a combination of surfactants selected from the group consisting of:
      i. anionic surfactants or combinations thereof selected from the group consisting of sodium, magnesium, ammonium and mono-, di- and triethanol amine salts of alkyl ether sulfates, N-alkoyl sarcosinates, alkyl phosphates, and alkyl ether phosphates;
      ii. nonionic surfactants or combinations thereof selected from aliphatic ($C_8$–$C_{18}$) primary or secondary, linear or branched chain alcohols and phenols condensed with 6 to 30 alkylene oxide units and mono and diallyl alkanolamides or alkyl polyglucosides;
      iii. amphoteric surfactants or combinations thereof; and
      iv. mixtures thereof.

13. The aqueous composition of claim 12 wherein component (b) is present in an amount of 1 to 40% by weight of the total composition.

14. The aqueous composition of claim 12 wherein the average particle size of the silicone material present in the emulsion is between 20 and 50 microns.

15. The aqueous composition of claim 12 wherein the preformed emulsion has an emulsifier HLB value between 3 and 8.

16. A method of making an aqueous composition comprising mixing together
   (a) a preformed emulsion formed by: combining and forming a homogeneous mixture of the following at a temperature of between 75° to 85° C.:
      i. 70 to 95%, by weight of the composition, of water
      ii. 1 to 5%, by weight of the composition, of sorbitan stearate, sorbitan distearate or mixtures thereof;
      iii. 0.001 to 1%, by weight of the composition, of stearyl alcohol ethylene oxide condensate having at least 50 and does not exceed 130 moles of ethylene oxide per mole of stearyl alcohol; then cooling the mixture to a temperature of between 25° to 75° C. and admixing
      iv. 0.01 to 10%, by weight of the composition, of an insoluble, non-volatile silicone; and
   (b) a surfactant or a combination of surfactants selected from the group consisting of:
      i. anionic surfactants or combinations thereof selected from the group consisting of sodium, magnesium, ammonium and mono-, di- and triethanol amine salts of alkyl ether sulfates, N-alkoyl sarcosinates, alkyl phosphates, and alkyl ether phosphates;
      ii. nonionic surfactants or combinations thereof selected from aliphatic ($C_8$–$C_{18}$) primary or secondary, linear or branched chain alcohols and phenols condensed with 6 to 30 alkylene oxide units and mono and diallyl alkanolamides or alkyl polyglucosides;
      iii. amphoteric surfactants or combinations thereof; and
      iv. mixtures thereof.

17. A method of making an aqueous composition comprising mixing together
   (a) 65 to 75% by weight of a pre-formed emulsion formed by: combining and forming a homogeneous mixture of the following at a temperature of about 80° C.:
      i. 90 to 92%, by weight of the emulsion, of water
      ii. 2 to 5%, by weight of the emulsion, of sorbitan stearate, sorbitan distearate or mixtures thereof;
      iii. 0.001 to 0.01%, by weight of the emulsion, of stearyl alcohol ethylene oxide condensate having at least 75 and does not exceed 110 moles of ethylene oxide per mole of stearyl alcohol; then cooling the mixture to a temperature of about 70° C. and admixing
      iv. 2 to 5%, by weight of the emulsion, of an insoluble, non-volatile silicone; and
   (b) 5 to 25%, by weight of the composition, of a surfactant or a combination of surfactants selected from the group consisting of:

i. anionic surfactants or combinations thereof selected from the group consisting of sodium, magnesium, ammonium and mono-, di- and triethanol amine salts of alkyl ether sulfates, N-alkoyl sarcosinates, alkyl phosphates, and alkyl ether phosphates;

ii. nonionic surfactants or combinations thereof selected from aliphatic ($C_8$–$C_{18}$) primary or secondary, linear or branched chain alcohols and phenols condensed with 6 to 30 alkylene oxide units and mono and diallyl alkanolamides or alkyl polyglucosides;

iii. amphoteric surfactants or combinations thereof selected from the group consisting of alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates, where alkyl and acyl groups have from 8 to 18 carbon atoms; and iv. mixtures thereof.

18. The method of claim 17 wherein the average particle size of the silicone material present in the emulsion is between 20 and 50 microns.

19. The method of claim 18 wherein the preformed emulsion has an emulsifier HLB value between 3 and 8.

20. The method of claim 17 wherein component:

(a) ii. is sorbitan monostearate;

(a) iii. is stearyl alcohol ethylene oxide condensate having 100 moles of ethylene oxide per mole of stearyl alcohol;

(a) iv. is dimethicone having a viscosity of from 5 to 500,000 centistokes at 25° C.

* * * * *

UNITED STATES PATENT AND TRADEMARK OFFICE
CERTIFICATE OF CORRECTION

PATENT NO. : 5,554,313
DATED : Sept. 10, 1996
INVENTOR(S) : John M. Chandler

It is certified that error appears in the above-identified patent and that said Letters Patent is hereby corrected as shown below:

Column 6, claim 1 at (c), line 37, "13" should be --130--.

Column 6, claim 1 at (e)ii., line 51, "60" should be --6--.

Column 6, claim 6, line 66, remove the second "of".

Column 7, claim 7, at (b)ii., line 28, "60" should be --6--.

Signed and Sealed this

Sixth Day of June, 2000

Attest:

Q. TODD DICKINSON

Attesting Officer

Director of Patents and Trademarks